(12) United States Patent
Seo et al.

(10) Patent No.: US 9,334,582 B2
(45) Date of Patent: May 10, 2016

(54) APPARATUS FOR EVALUATING QUALITY OF CRYSTAL, AND METHOD AND APPARATUS FOR MANUFACTURING SEMICONDUCTOR LIGHT-EMITTING DEVICE INCLUDING THE APPARATUS

(71) Applicant: Samsung Electronics Co., Ltd., Suwon-Si, Gyeonggi-Do (KR)

(72) Inventors: Jong-uk Seo, Suwon-si (KR); Byoung-kyun Kim, Seongnam-si (KR); Suk-ho Yoon, Seoul (KR); Keon-hun Lee, Seoul (KR); Kee-won Lee, Suwon-si (KR); Do-young Rhee, Seoul (KR); Sang-don Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/602,447

(22) Filed: Jan. 22, 2015

(65) Prior Publication Data
US 2015/0233821 A1    Aug. 20, 2015

(30) Foreign Application Priority Data

Feb. 17, 2014  (KR) .................. 10-2014-0018034

(51) Int. Cl.
| H01L 21/66 | (2006.01) |
| C30B 25/08 | (2006.01) |
| H01L 33/06 | (2010.01) |
| G01N 21/95 | (2006.01) |
| H01L 21/02 | (2006.01) |
| H01L 33/00 | (2010.01) |

(52) U.S. Cl.
CPC ............ *C30B 25/08* (2013.01); *G01N 21/9501* (2013.01); *H01L 33/06* (2013.01); *H01L 21/0254* (2013.01); *H01L 21/0262* (2013.01); *H01L 22/12* (2013.01); *H01L 33/007* (2013.01); *H01L 33/0075* (2013.01)

(58) Field of Classification Search
CPC ........ C30B 25/08; G01N 21/95; G01N 21/55; G01N 21/27; G01N 21/88; H01L 21/02; H01L 21/66
USPC ............... 438/16; 356/51, 416, 445; 118/712
See application file for complete search history.

(56) References Cited

U.S. PATENT DOCUMENTS

| 4,352,016 | A | * | 9/1982 | Duffy ..................... G01N 21/55 250/358.1 |
| 4,511,800 | A | * | 4/1985 | Harbeke ............... G01B 11/303 250/358.1 |
| 6,372,608 | B1 | | 4/2002 | Shimoda et al. |
| 6,645,830 | B2 | | 11/2003 | Shimoda et al. |
| RE38,466 | E | | 3/2004 | Inoue et al. |
| 6,818,465 | B2 | | 11/2004 | Biwa et al. |
| 6,818,530 | B2 | | 11/2004 | Shimoda et al. |

(Continued)

FOREIGN PATENT DOCUMENTS

| JP | 2011251905 A | 12/2011 |
| KR | 10-2012-0079393 A | 7/2012 |

*Primary Examiner* — Caleb Henry
(74) *Attorney, Agent, or Firm* — Harness, Dickey & Pierce, P.L.C.

(57) ABSTRACT

An apparatus for evaluating the quality of a crystal includes an optical device that measures a surface reflectance of a wafer in which a V-pit is formed; and a data processing unit that calculates a threading dislocation density by calculating a difference in surface reflectance of the wafer that is measured by the optical device.

6 Claims, 12 Drawing Sheets

(56) References Cited

U.S. PATENT DOCUMENTS

| | | |
|---|---|---|
| 6,858,081 B2 | 2/2005 | Biwa et al. |
| 6,967,353 B2 | 11/2005 | Suzuki et al. |
| 7,002,182 B2 | 2/2006 | Okuyama et al. |
| 7,084,420 B2 | 8/2006 | Kim et al. |
| 7,087,932 B2 | 8/2006 | Okuyama et al. |
| 7,154,124 B2 | 12/2006 | Han et al. |
| 7,208,725 B2 | 4/2007 | Sherrer et al. |
| 7,288,758 B2 | 10/2007 | Sherrer et al. |
| 7,319,044 B2 | 1/2008 | Han et al. |
| 7,501,656 B2 | 3/2009 | Han et al. |
| 7,655,197 B2 | 2/2010 | Vaudo et al. |
| 7,709,857 B2 | 5/2010 | Kim et al. |
| 7,732,306 B2 | 6/2010 | Arena et al. |
| 7,759,140 B2 | 7/2010 | Lee et al. |
| 7,776,152 B2 | 8/2010 | Hoke et al. |
| 7,781,727 B2 | 8/2010 | Sherrer et al. |
| 7,790,482 B2 | 9/2010 | Han et al. |
| 7,915,152 B2 | 3/2011 | Vaudo et al. |
| 7,940,350 B2 | 5/2011 | Jeong |
| 7,959,312 B2 | 6/2011 | Yoo et al. |
| 7,964,881 B2 | 6/2011 | Choi et al. |
| 7,985,976 B2 | 7/2011 | Choi et al. |
| 7,994,525 B2 | 8/2011 | Lee et al. |
| 8,008,683 B2 | 8/2011 | Choi et al. |
| 8,013,352 B2 | 9/2011 | Lee et al. |
| 8,049,161 B2 | 11/2011 | Sherrer et al. |
| 8,129,711 B2 | 3/2012 | Kang et al. |
| 8,179,938 B2 | 5/2012 | Kim |
| 8,188,458 B2 | 5/2012 | Craven et al. |
| 8,212,259 B2 | 7/2012 | Flynn et al. |
| 8,263,987 B2 | 9/2012 | Choi et al. |
| 8,324,646 B2 | 12/2012 | Lee et al. |
| 8,329,565 B2 | 12/2012 | Arena et al. |
| 8,368,179 B2 | 2/2013 | Kaeding et al. |
| 8,399,944 B2 | 3/2013 | Kwak et al. |
| 8,432,511 B2 | 4/2013 | Jeong |
| 8,459,832 B2 | 6/2013 | Kim |
| 8,502,242 B2 | 8/2013 | Kim |
| 8,536,604 B2 | 9/2013 | Kwak et al. |
| 8,735,931 B2 | 5/2014 | Han et al. |
| 8,766,295 B2 | 7/2014 | Kim |
| 2002/0115228 A1* | 8/2002 | Kiyota ................. G01N 21/956 438/7 |
| 2003/0070610 A1 | 4/2003 | Dadgar et al. |
| 2007/0122990 A1* | 5/2007 | Tanaka ............. H01L 21/02057 438/357 |
| 2007/0218703 A1* | 9/2007 | Kaeding ............... C30B 23/025 438/775 |
| 2007/0222962 A1* | 9/2007 | Kudo ................... G02B 27/288 355/71 |
| 2007/0279080 A1* | 12/2007 | Ohtsuki ............. G01R 31/2889 324/750.14 |
| 2008/0273185 A1* | 11/2008 | Omura .................... G03B 27/54 355/67 |
| 2009/0098343 A1 | 4/2009 | Arena et al. |
| 2011/0276299 A1* | 11/2011 | Nemoto ............. G01N 21/9501 702/104 |
| 2011/0316000 A1 | 12/2011 | Beaumont et al. |
| 2012/0187444 A1 | 7/2012 | Oh et al. |
| 2013/0010296 A1* | 1/2013 | Kwak .................. G01N 21/211 356/369 |
| 2013/0337601 A1* | 12/2013 | Kapur ............. H01L 31/06875 438/93 |
| 2014/0175461 A1* | 6/2014 | Momose ................ C30B 25/20 257/77 |
| 2014/0204383 A1* | 7/2014 | Sopori ............... G01N 21/8901 356/416 |
| 2015/0168311 A1* | 6/2015 | Seki ................... G01N 21/6489 356/51 |

\* cited by examiner

APPARATUS FOR EVALUATING QUALITY OF CRYSTAL, AND METHOD AND APPARATUS FOR MANUFACTURING SEMICONDUCTOR LIGHT-EMITTING DEVICE INCLUDING THE APPARATUS

CROSS-REFERENCE TO RELATED APPLICATIONS

This application claims the benefit of priority from Korean Patent Application No. 10-2014-0018034, filed on Feb. 17, 2014, in the Korean Intellectual Property Office, the disclosure of which is incorporated herein in its entirety by reference.

BACKGROUND

The inventive concepts relate to an apparatus for evaluating quality of crystal, a method and apparatus for manufacturing a semiconductor light-emitting device including the apparatus, a semiconductor light-emitting device manufactured by the method, and/or an apparatus for evaluating quality of crystal, whereby the threading dislocation density (TDD) of a wafer for a semiconductor light-emitting device may be calculated.

Quality of crystal of epitaxial wafers for semiconductor light-emitting devices implemented by epitaxial growth is a significant index that directly affects luminescent efficiency and a life span. In particular, in nitride-based semiconductor devices, controlling the quality of crystal of wafers for semiconductor light-emitting devices so as to reduce or prevent the deterioration of characteristics or reliability of a semiconductor product due to high TDD helps maintain and enhance the characteristics and reliability of the semiconductor product.

SUMMARY

The inventive concepts provide an apparatus for evaluating quality of crystal that may reduce or prevent the deterioration of characteristics or reliability of a nitride-based semiconductor light-emitting device, a method and apparatus for manufacturing a semiconductor light-emitting device including the apparatus, and/or a semiconductor light-emitting device manufactured by the method.

According to at least one example embodiment, a method of manufacturing a semiconductor light-emitting device includes growing a wafer so that a surface feature such as a notch or a V-pit is formed in one or more layers of the wafer for a semiconductor light-emitting device having a first conductive layer, an active layer, and a second conductive layer, measuring a surface reflectance of one or more layers selected from the first conductive layer, the active layer, and the second conductive layer of the wafer using an optical device in the growing of the wafer, and evaluating the quality of crystal by calculating a difference of the measured surface reflectance and by calculating the threading dislocation density of the wafer.

The measuring of the surface reflectance may include radiating incident light onto the wafer and receiving reflected light from the wafer.

The measuring of the surface reflectance may further include changing a path of the incident light or of the reflected light, or focusing the incident light or the reflected light.

The incident light may belong to a wavelength area in which no Fabry-Perot interference occurs.

The incident light may have a short wavelength.

A wavelength of the incident light may be substantially between 300 nm and 420 nm.

The evaluating of the quality of crystal may include measuring a surface reflectance of the wafer in a particular time interval and calculating a threading dislocation density of the wafer by using the difference in the surface reflectance collected in the particular time interval.

According to another example embodiment, an apparatus for manufacturing a semiconductor light-emitting device includes a growth chamber in which a wafer is grown so that a surface feature such as a notch or a V-pit is formed in one or more layers of the wafer for a semiconductor light-emitting device including a first conductive layer, an active layer, and a second conductive layer, and an apparatus for evaluating the quality of crystal that evaluates a quality of crystal of the wafer by measuring a surface reflectance of one or more layers selected from the first conductive layer, the active layer, and the second conductive layer of the wafer, wherein the apparatus for evaluating quality of crystal includes an optical device configured to measure a surface reflectance of one layer of the wafer and a data processing unit configured to calculate a threading dislocation density by calculating a difference in surface reflectance of the one layer of the wafer that is measured by the optical device.

The optical device may include a light-emitting unit configured to radiate an incident light onto the wafer and a light-receiving unit configured to receive reflected light from the wafer, and the light-emitting unit may be configured to radiate incident light perpendicular to a growth surface of the wafer.

The data processing unit may include a first processing unit configured to collect a surface reflectance of the wafer in a particular time interval and to measure a total difference in surface reflectance in the particular time interval, thereby calculating the density of a V-pit formed in the wafer.

The data processing unit may further include a second processing unit configured to calculate a threading dislocation density by using the density of the V-pit that is calculated by the first processing unit.

The apparatus for evaluating quality of crystal may be configured to determine the quality of crystal of the wafer in real-time while the wafer is grown in the growth chamber.

The apparatus for evaluating quality of crystal may be configured to operate only in one or more particular time intervals in which the wafer is grown in the growth chamber.

The apparatus for evaluating quality of crystal may be configured to operate only in a particular time interval until a V-pit is intentionally formed, among the time intervals during which the wafer is grown in the growth chamber and in a particular time interval in which a V-pit is intentionally formed.

The data processing unit may be configured to calculate a threading dislocation density by using a difference between surface reflectance measured in the particular time interval until a V-pit is intentionally formed, among the time intervals during which the wafer is grown in the growth chamber and in a particular time interval during which a V-pit is intentionally formed.

BRIEF DESCRIPTION OF THE DRAWINGS

Example embodiments of the inventive concepts will be more clearly understood from the following detailed description taken in conjunction with the accompanying drawings in which.

DETAILED DESCRIPTION

Figure 1:
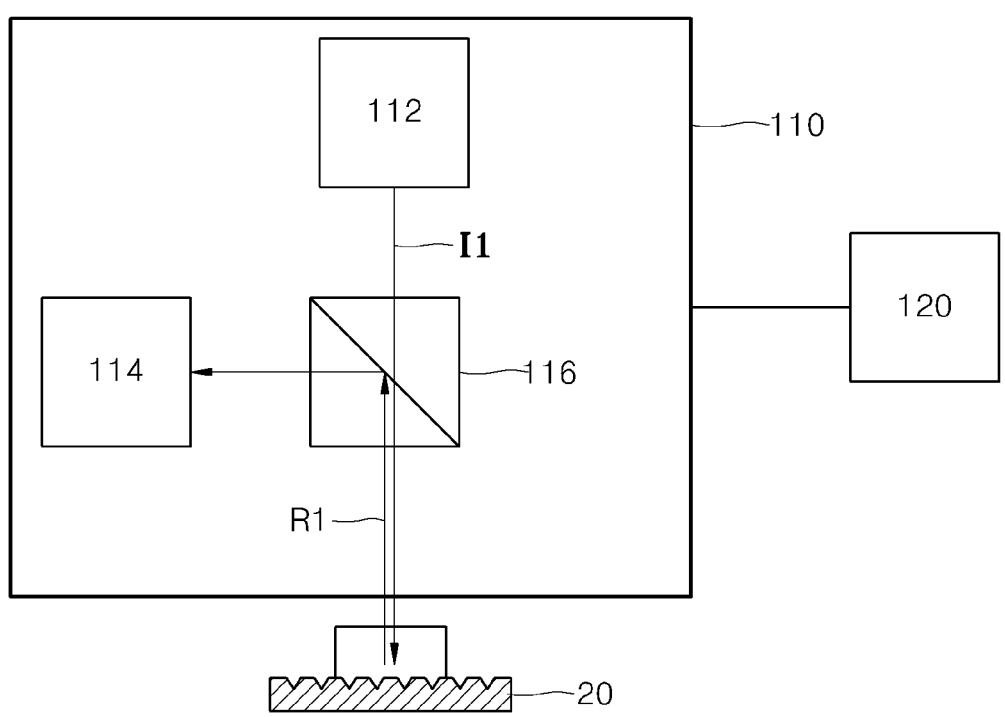
FIG. 1 schematically illustrates part of a configuration of an apparatus for evaluating quality of crystal, according to an example embodiment.

Example embodiments of the inventive concepts will be described more fully with reference to the accompanying drawings. The example embodiments will now be described more fully with reference to the accompanying drawings. The invention may, however, be embodied in many different forms and should not be construed as being limited to the example embodiments set forth herein; rather, these example embodiments are provided so that this disclosure will be thorough and complete, and will fully convey the inventive concepts to those skilled in the art. In the drawings, like reference numerals refer to like elements. In the accompanying drawings, sizes of structures are enlarged or reduced compared to actual sizes for clarity of the inventive concepts.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", "third", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the example embodiment. For example, a first component may be referred to as a second component without deviating from the scope of the example embodiment, and similarly, a second component may be referred to as a first component.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

When a certain embodiment may be implemented differently, a specific process order may be performed differently from the described order. For example, two consecutively described processes may be performed substantially at the same time or performed in an order opposite to the described order.

In the drawings, for example, illustrated shapes may be deformed according to fabrication technology and/or tolerances. Therefore, the exemplary embodiments of the inventive concepts are not limited to certain shapes illustrated in the present specification, and may include modifications of shapes caused in fabrication processes. Expressions such as "at least one of," when preceding a list of elements, modify the entire list of elements and do not modify the individual elements of the list.

In the drawing figures, the dimensions of layers and regions may be exaggerated for clarity of illustration. Like reference numerals refer to like elements throughout. The same reference numbers indicate the same components throughout the specification.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

FIG. 1 schematically illustrates part of a configuration of an apparatus 100 for evaluating the quality of a crystal, according to an example embodiment.

Referring to FIG. 1, the apparatus 100 for evaluating the quality of a crystal includes an optical device 110 and a data processing unit 120 configured to process data received from the optical device 110.

Figure 7A:
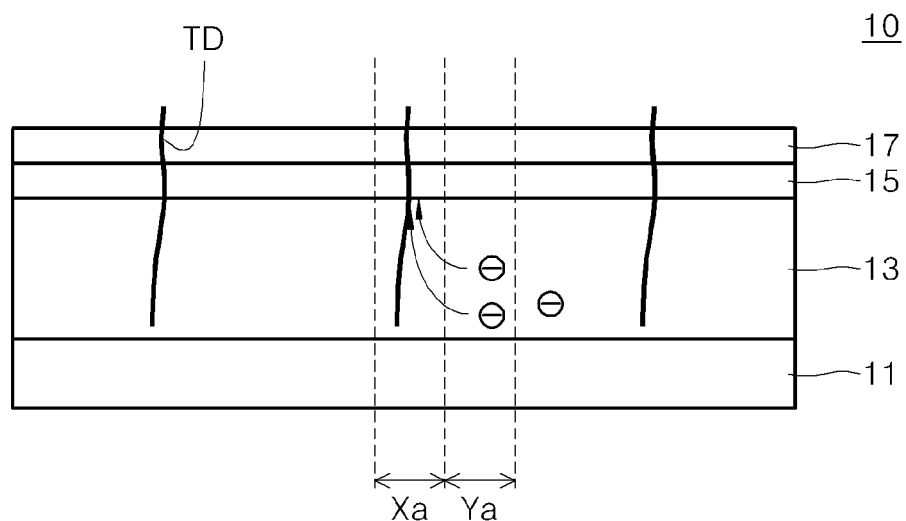
FIGS. 7A and 7B are schematic views illustrating why a V-pit is formed when a nitride-based semiconductor is grown, according to at least one example embodiment.
Figure 7B:
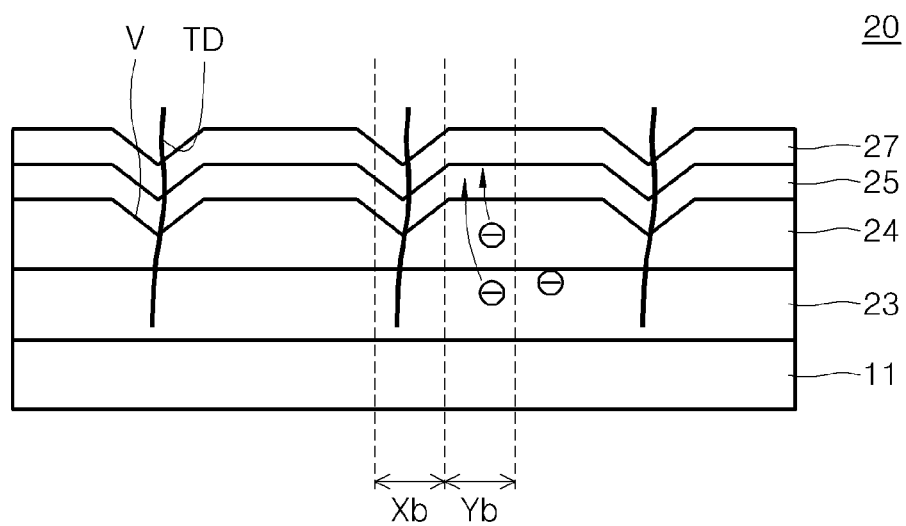

According to at least one example embodiment, the optical device 110 is configured to perform a function of measuring the surface reflectance of a wafer 20 for a semiconductor light-emitting device which, as illustrated in FIG. 7B, includes a first conductive layer 23, an active layer 25, and a second conductive layer 27 and in which a surface feature such as a notch or a V-pit is formed on at least one of the first conductive layer 23, the active layer 25, and the second conductive layer 27. A more detailed description of the wafer 20 is provided with reference to FIG. 7B. In some example embodiments, the optical device 110 includes a light-emitting unit 112 configured to radiate incident light I1 onto the wafer 20, a light-receiving unit 114 configured to receive reflected light R1 reflected from the wafer 20, and a light-processing unit 116 configured to change a path of the incident light I1 radiated by the light-emitting unit 112 or a path of the reflected light R1 reflected from the wafer 20 or to focus the incident light I1 and the reflected light R1.

In some example embodiments, the optical device 110 measures reflectance by comparing a quantity of incident light I1 radiated by the light-emitting unit 112 onto the wafer 20 with a quantity of reflected light R1 reflected from a surface of the wafer 20. A technique, in which a standard wafer (not shown) having well-known optical characteristics is disposed instead of the wafer 20 and a quantity of reflected light from a surface of the standard wafer is measured, may be used to measure the quantity of incident light I1 radiated onto the wafer 20 by the light-emitting unit 112. Since the reflectance of the optical characteristics of the standard wafer is also well known, the quantity of incident light I1 radiated onto the wafer 20 by the light-emitting unit 112 may be calculated using the measured quantity of reflected light and the reflectance of the standard wafer.

In some example embodiments, the light-emitting unit 112 may use a laser diode (LD) or a light-emitting diode (LED) as a light source. However, example embodiments are not limited thereto, and the light-emitting unit 112 may include one of various sources, such as a halogen lamp, a xenon (Xe) arc lamp, and a deuterium lamp, as the light source.

The incident light I1 radiated by the light-emitting unit 112 passes through the light-processing unit 116 and is transferred to the wafer 20. In some example embodiments, the incident light I1 radiated by the light-emitting unit 112 may include near ultraviolet rays having a wavelength between about 300 nm and about 420 nm. In another example embodiment, the incident light I1 radiated by the light-emitting unit 112 may include visible rays having a wavelength between about 420 nm and about 700 nm.

According to at least one example embodiment, the incident light I1 radiated by the light-emitting unit 112 may have a single wavelength. However, even when the incident light I1 radiated by the light-emitting unit 112 has one or more wavelengths, only light having a single wavelength may reach the wafer 20 by using a spectrometer (not shown) that may separate or extract light according to wavelength. The spectrometer may be interposed between the light-emitting unit 112 and the light-processing unit 116 or may be included in the light-processing unit 116. In some example embodiments, the light-emitting unit 112 may be configured to radiate the incident light I1 having a wavelength area in which no Fabry-Perot interference occurs.

In some example embodiments, the light-emitting unit 112 may configured to radiate the incident light I1 perpendicularly to a surface of the wafer 20. In this case, only the reflected light R1 reflected in a direction parallel to the incident light I1 among the light reflected from the surface of the wafer 20 passes through the light-processing unit 116 and reaches the light-receiving unit 114. That is, light scattered from the surface of the wafer 20 may not reach the light-receiving unit 114, and a detailed description thereof will be provided with reference to FIGS. 6A and 6B.

The light-processing unit 116 may be configured to perform a function of changing a path of the incident light I1 radiated by the light-emitting unit 112 or a path of the reflected light R1 reflected from the wafer 20 or focusing the incident light I1 or the reflected light R1. The light-processing unit 116 according to an example embodiment may be configured to perform only a function of a half mirror that causes the incident light I1 to pass through the light-processing unit 116 and to reflect the reflected light R1. However, example embodiments are not limited thereto, and the light-processing unit 116 may further include a spectrometer configured to separate and extract light according to a wavelength.

The data processing unit 120 may be configured to calculate threading dislocation density (TDD) by calculating a difference in surface reflectance of the wafer 20, which is measured by the optical device 110.

In some example embodiments, the data processing unit 120 may be configured to collect the surface reflectance of the wafer 20 that is measured by the optical device 110 in a particular time interval and to calculate TDD of the wafer 20 by using the total difference in surface reflectance of the wafer 20 in the particular time interval. A technique for calculating TDD of the wafer 20 by using the difference in surface reflectance of the wafer 20 over time will be described later with reference to FIGS. 4A through 7.

Figure 2:
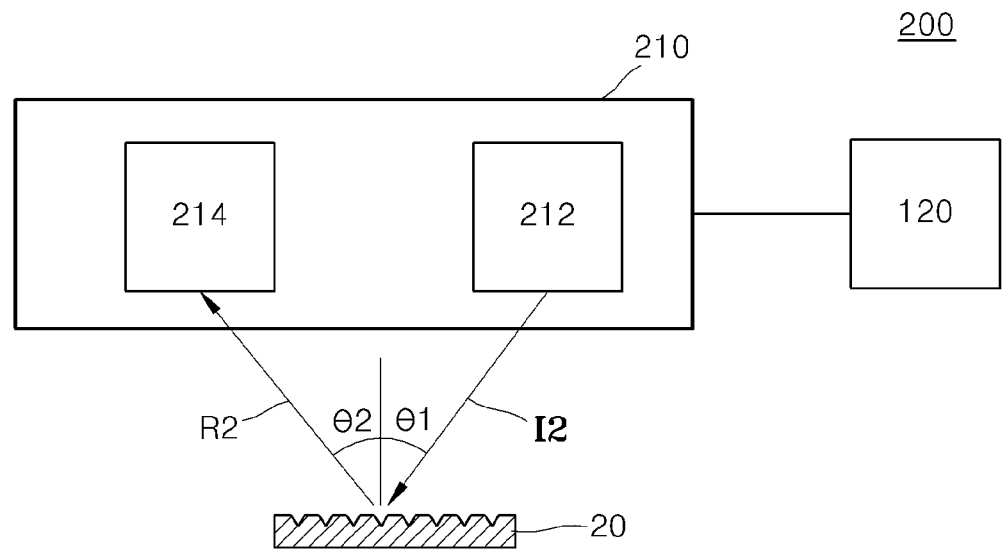
FIG. 2 schematically illustrates part of a configuration of an apparatus for evaluating the quality of the crystal, according to another example embodiment.

FIG. 2 schematically illustrates part of a configuration of an apparatus 200 for evaluating quality of crystal, according to another example embodiment. In FIG. 2, like reference numerals that are the same as those of FIG. 1 represent like elements, and for simplicity of explanation, a redundant description thereof will be omitted.

Referring to FIG. 2, the apparatus 200 for evaluating quality of crystal includes an optical device 210 and a data processing unit 120 configured to process data received from the optical device 210.

The optical device 210 is configured to measure the surface reflectance of a wafer 20. In some example embodiments, the optical device 210 includes a light-emitting unit 212 configured to radiate incident light I2 onto the wafer 20 and a light-receiving unit 214 configured to receive reflected light R2 reflected from the wafer 20.

In some example embodiments, the optical device 210 is configured to measure reflectance by comparing a quantity of incident light I2 radiated by the light-emitting unit 212 onto the wafer 20 with a quantity of reflected light R2 reflected from a surface of the wafer 20. A technique using a standard wafer (not shown), as described above with reference to FIG. 1, may be used to measure the quantity of incident light I2 radiated onto the wafer 20 by the light-emitting unit 212. In this way, the quantity of incident light I2 radiated onto the wafer 20 by the light-emitting unit 212 may be calculated using the measured quantity of reflected light and the reflectance of the standard wafer.

In some example embodiments, the light-emitting unit 212 may include an LD or LED as a light source. However, example embodiments are not limited thereto, and the light-emitting unit 212 may include one of various sources, such as a halogen lamp, an Xe arc lamp, and a deuterium lamp, among others, as the light source.

According to at least one example embodiment, the incident light I2 radiated by the light-emitting unit 212 is transferred to the wafer 20 at an incidence angle θ1. The incidence angle θ1 is defined as an angle of the incident light I2 with respect to a direction (normal direction) perpendicular to the surface of the wafer 20.

The reflected light R2 reflected from the wafer 20 is transferred to the light-receiving unit 214 at a reflection angle θ2. The reflection angle θ2 is defined as an angle of the reflected light R2 with respect to a direction (normal direction) perpendicular to the surface of the wafer 20. In this case, only the reflected light R2 reflected at a reflection angle that is the same as the incidence angle θ1 of the incident light I2 among light reflected from the surface of the wafer 20 reaches the light-receiving unit 214. That is, only the reflected light R2 of which the reflection angle θ2 is the same as the incidence angle θ1 reaches the light-receiving unit 214, and light scattered from the surface of the wafer 20 does not reach the light-receiving unit 214.

In some example embodiments, the incident light I2 radiated by the light-emitting unit 212 may include near ultraviolet rays having a wavelength between about 300 nm and about 420 nm. In another example embodiment, the incident light I2 radiated by the light-emitting unit 212 may include visible rays having a wavelength between about 420 nm and about 700 nm. On the other hand, the incident light I2 radiated by the light-emitting unit 212 may have a single wavelength. However, even when the incident light I2 radiated by the light-emitting unit 212 has one or more wavelengths, only light having a single wavelength may reach the wafer 20 because of a spectrometer (not shown) that may separate or extract light according to a wavelength. The spectrometer may be interposed between the light-emitting unit 212 and the wafer 20. In some example embodiments, the light-emitting unit 212 may radiate the incident light I2 having a wavelength area in which no Fabry-Perot interference occurs.

The data processing unit 120 is configured to calculate TDD by calculating a difference in surface reflectance of the wafer 20, which is measured by the optical device 210. Since a detailed description of the data processing unit 120 has been provided with reference to FIG. 1, for simplicity of explanation, a redundant description thereof will be omitted.

Figure 3:
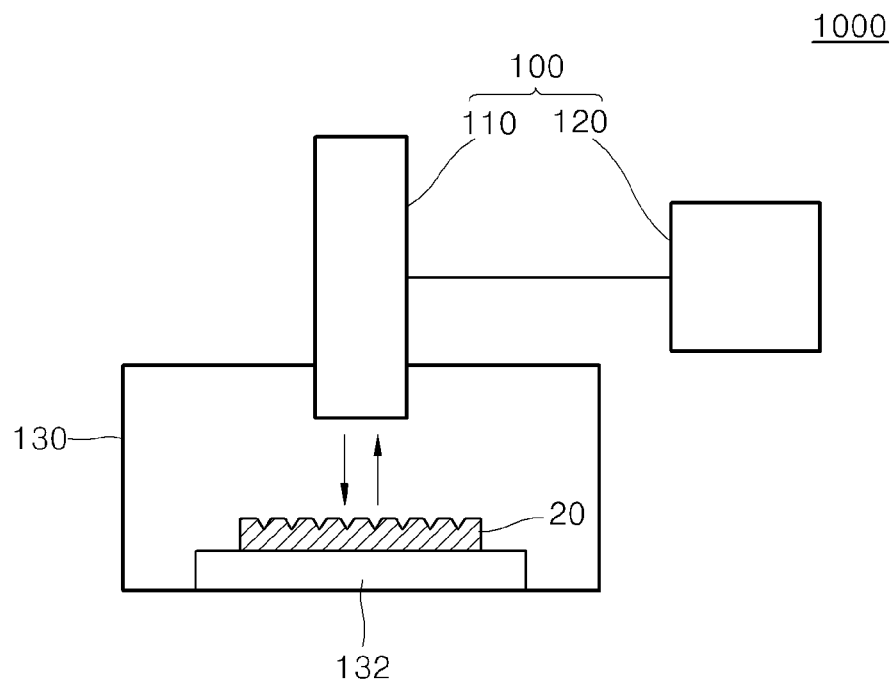
FIG. 3 schematically illustrates part of a configuration of an apparatus for manufacturing a semiconductor light-emitting device including the apparatus for evaluating the quality of the crystal, according to an example embodiment.

FIG. 3 schematically illustrates part of a configuration of an apparatus 1000 for manufacturing a semiconductor light-emitting device including the apparatus for evaluating quality of crystal, according to an example embodiment of the inventive concepts. In FIG. 3, like reference numerals that are the same as those of FIGS. 1 and 2 represent like elements, and for simplicity of explanation, a redundant description thereof will be omitted.

Referring to FIG. 3, the example apparatus 1000 for manufacturing a semiconductor light-emitting device includes an apparatus 100 configured to evaluate the quality of the crystal and a growth chamber 130 that is connected to an optical device 110 of the apparatus 100 for evaluating quality of crystal.

The apparatus 100 for evaluating quality of crystal includes the optical device 110 and a data processing unit 120 configured to process data received from the optical device 110. In some example embodiments, the optical device 110 of the apparatus 100 for evaluating quality of crystal is disposed to correspond to a growth surface of the wafer 20 and is configured to evaluate the quality of crystal of the wafer 20 being grown.

In some example embodiments, the apparatus 100 for evaluating the quality of the crystal measures the surface reflectance of one or more layers selected from a first conductive layer (e.g., layer 23 of FIG. 7B), an active layer 25, and a second conductive layer 27 of the wafer 20 that is being grown in the growth chamber 130, and evaluates the quality of the crystal of the wafer 20 in real-time.

In another example embodiment, the apparatus 100 for evaluating the quality of the crystal may operate only one or more times selected from times at which the wafer 20 is grown in the growth chamber 130. For example, the apparatus 100 for evaluating quality of crystal may operate only in a particular time interval (T1 of FIG. 4A) until a V-pit is intentionally formed, among time intervals in which the wafer 20 is grown in the growth chamber 130 and in a particular time interval (a particular time interval selected from T1_1 to T1_5 of FIG. 4A) in which a V-pit is intentionally formed.

The optical device 110 in the example embodiment is disposed above the growth chamber 130. However, example embodiments are not limited thereto, and the optical device 110 may be disposed at a side of the growth chamber 130. Also, as illustrated in FIG. 3, part of the optical device 110 may not be disposed in the growth chamber 130 but may be spaced apart from the growth chamber 130 (not shown). In this case, incident light and reflected light of the optical device 110 move through a transparent window (not shown) installed at the growth chamber 130.

In some example embodiments, the growth chamber 130 includes a wafer chuck 132 that supports the wafer 20 while the wafer 20 is grown. Although not shown, the growth chamber 130 may further include a gas supply pipe, a gas exhaust pipe, and a heating unit in addition to the wafer chuck 132.

In some example embodiments, the data processing unit 120 may include a first processing unit (not shown) that collects the surface reflectance of the wafer 20 in a particular time interval and measures the total difference in surface reflectance in the particular time interval, thereby calculating the density of a V-pit formed in the wafer 20. A description of a technique for calculating the density of a V-pit may be referred to with reference to FIGS. 4A and 4B.

In some example embodiments, the data processing unit 120 may further include a second processing unit (not shown) configured to calculate TDD using the density of the V-pit that is calculated by the first processing unit. A description of a technique for calculating TDD may be referred to with reference to FIG. 5.

In the growth chamber 130, the wafer 20 is grown in such a way that a V-pit may be formed in one or more layers of the wafer 20 such as the first conductive layer (e.g., layer 23 of FIG. 7B), the active layer 25, and the second conductive layer 27. The wafer 20 may be a wafer for a nitride-based semiconductor, such as GaN. Since steam pressure of nitrogen is very high near a melting point of GaN (exceeding 2000° C.) and it is typically difficult to grow a crystal of GaN by using a melt growth technique, such as a Czochralski method, other techniques, such as metal organic chemical vapor deposition (MOCVD), molecular beam epitaxy (MBE), and hydride vapor phase epitaxy (HVPE), are used to manufacture the nitride-based semiconductor.

An MOCVD technique is a representative vapor layer formation technique. In the MOCVD technique, a group III organic metal, such as gallium, is vaporized, is thermally decomposed on a surface of a substrate, and then reacts with a group V gas, thereby forming a layer. In the MOCVD technique, a thickness or composition of a layer may be controlled, and high productivity may be achieved. Thus, the MOCVD technique is typically widely used as a layer formation technique when a nitride-based semiconductor is manufactured. An MOCVD device may include the growth chamber 130, the wafer chuck 132 disposed in the growth chamber 130, and a gas passage (not shown) for a reaction gas to flow onto the surface of the wafer 20. In the MOCVD device, the wafer 20 is stacked on the wafer chuck 132, the growth chamber 130 is depressurized, the wafer 20 is heated at an appropriate temperature and passes through the gas passage so that gas of the organic metal is introduced to the surface of the wafer 20 so that a layer may be formed.

The MBE technique has advantages of excellent thin layer characteristics, low-temperature growth, and real-time process monitoring. The principle of the MBE technique is that a good-quality material is grown on the wafer 20 using metal flux and plasma in a high-vacuum and high-temperature environment. The MBE technique may be classified as including two types according to a method of activating nitrogen. The first method is a method of using high temperature cracking of ammonia similarly in the above-described MOCVD technique, and the second method is a technique, i.e., PA MBE (plasma assisted MBE), which includes activation of atomic nitrogen in plasma generated in a remote plasma source (nitrogen activator). A common advantage of the two MBE types is relatively lower material consumption and a lower epitaxial growth temperature, compared to the MOCVD technique. In addition to an economical advantage, a low gas pressure in the growth chamber 130 may prevent a parasitic gas reaction.

The HVPE technique produces relatively poor characteristics to an epitaxy grown film, compared to the above-described MOCVD or MBE technique. However, in the HVPE technique, a low-priced nitride-based semiconductor may be reduced, and growth speed is high so that the HVPE technique is advantageous for growing a thick layer on a substrate. An HVPE device includes a gas supply pipe (not shown) that supplies gallium chloride ($GaCl_3$) gas into the growth chamber 130, a gas supply pipe (not shown) that supplies ammonia ($NH_3$) gas into the growth chamber 130, and the wafer chuck 132 in the growth chamber 130. The $GaCl_3$ gas and the $NH_3$ gas that are injected into the growth chamber 130 via a gas supply pipe react with each other so that gallium nitride (GaN) may be grown on the wafer 20.

When the nitride-based semiconductor is manufactured using the MOCVD technique, the MBE technique, or the HVPE technique, the quality of the grown crystal of the wafer 20 may be controlled using the apparatus 100 for evaluating quality of crystal according to the example embodiments. Thus, the deterioration of the characteristics or reliability of a semiconductor product may be prevented or reduced due to high TDD of the nitride-based semiconductor, and the characteristics and reliability of the semiconductor product may be maintained and enhanced.

Figure 4A:
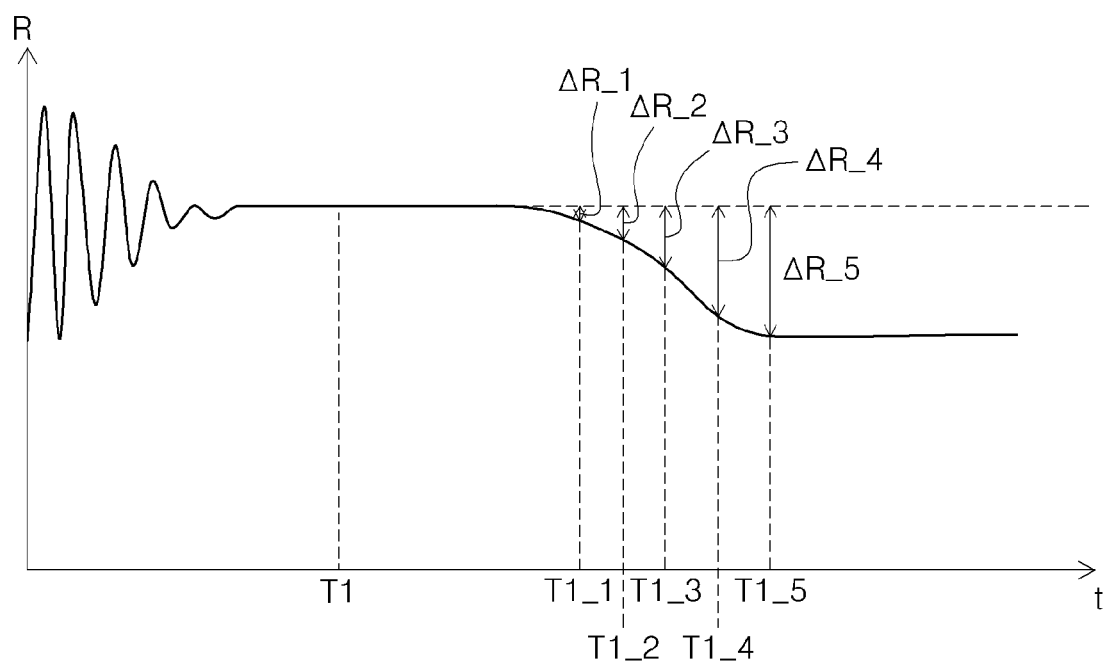
FIG. 4A is a graph showing a change in surface reflectance of a wafer over time, according to at least one example embodiment.

FIG. 4A is a graph showing a change in surface reflectance of a wafer over time. In FIG. 4A, the X-axis represents time t and the Y-axis represents surface reflectance R of a wafer.

Figure 4B:
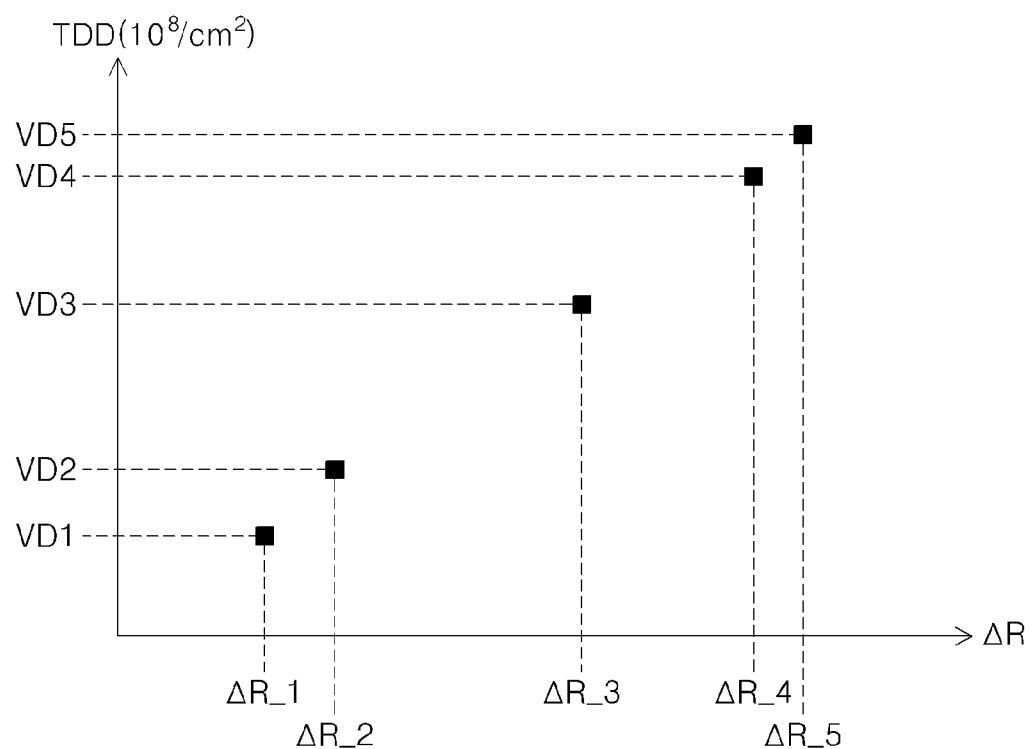
FIG. 4B is a graph showing the correlation between a difference in surface reflectance of a wafer and surface feature such as a notch or a V-pit density, according to at least one example embodiment.

FIG. 4B is a graph showing the correlation between a difference in surface reflectance of a wafer and V-pit density. In FIG. 4B, the X-axis represents a difference in reflectance $\Delta R$, and the Y-axis represents the V-pit density VD. In FIGS. 4A and 4B, like reference numerals that are the same as those of FIGS. 1 through 3 represent like elements, and for simplicity of explanation, a redundant description thereof will be omitted.

Referring to FIGS. 4A and 4B, surface reflectance R of the wafer 20 is reduced in time intervals from T1 to T1_5 while the wafer 20 is grown.

In some example embodiments, T1 is a particular time interval after which a V-pit is intentionally formed, among time intervals in which the wafer 20 is grown in the growth chamber 130, and T1_1, T1_2, T1_3, T1_4, and T1_5 are particular time intervals in which a V-pit is intentionally formed, among time intervals in which a V-pit is intentionally formed, among time intervals in which the wafer 20 is grown in the growth chamber 130.

In detail, a first reflectance difference $\Delta R\_1$ is a difference between surface reflectance at T1 and surface reflectance at T1_1. Similarly, a second reflectance difference $\Delta R\_2$ is a difference between a surface reflectance at T1 and a surface reflectance at T1_2, and a third reflectance difference $\Delta R\_3$ is a difference between the surface reflectance at T1 and a surface reflectance at T1_3, and a fourth reflectance difference $\Delta R\_4$ is a difference between the surface reflectance at T1 and a surface reflectance at T1_4, and a fifth reflectance difference $\Delta R\_5$ is a difference between the surface reflectance at T1 and a surface reflectance at T1_5.

A first V-pit density VD1 is the V-pit density of the wafer 20 at a time interval that corresponds to the first reflectance difference ΔR_1. That is, the first V-pit density VD1 is the V-pit density of the wafer 20 at T1_1. Similarly, second through fifth V-pit densities VD2, VD3, VD4, and VD5 are V-pit densities of the wafer 20 at time intervals T1_2, T1_3, T1_4, and T1_5 that correspond to the second through fifth reflectance differences ΔR_2, ΔR_3, ΔR_4, and ΔR_5.

In terms of the relationship between the first through fifth reflectance differences ΔR_1, ΔR_2, ΔR_3, ΔR_4, and ΔR_5 and the first through fifth V-pit densities VD1, VD2, VD3, VD4, and VD5 that are obtained through experiments, the first V-pit density VD1 when the first reflectance difference ΔR_1 is 1.22, is $1.22 \times 10^8/cm^2$, the second V-pit density VD2 when the second reflectance difference ΔR_2 is 1.80, is $2.53 \times 10^8/cm^2$, the third V-pit density VD3 when the third reflectance difference ΔR_3 is 3.80, is $5.12 \times 10^8/cm^2$, the fourth V-pit density VD4 when the fourth reflectance difference ΔR_4 is 5.20, is $7.13 \times 10^8/cm^2$, and the fifth V-pit density VD5 when the fifth reflectance difference ΔR_5 is 5.60, is $7.78 \times 10^8/cm^2$. That is, the V-pit density VD may be in proportion to the reflectance difference ΔR (Equation 1). k1 in Equation 1 is a constant reflecting proportionality.

$$VD = k1 \cdot \Delta R \qquad [\text{Equation 1}]$$

From the correlation between the V-pit density VD and the reflectance difference ΔR, the data processing unit 120 may collect the surface reflectance of the wafer 20 in a particular time interval and may measure the total difference in surface reflectance in the particular time interval, thereby calculating the density of a V-pit formed in the wafer 20.

Figure 5:
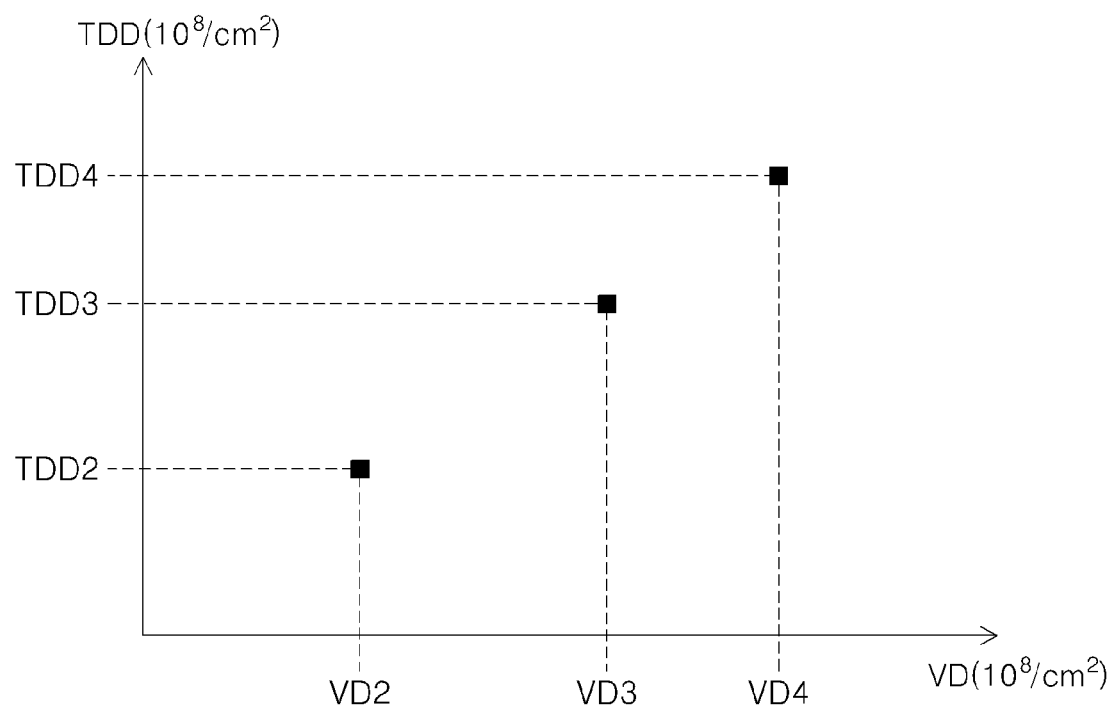
FIG. 5 is a graph showing the correlation between V-pit density and threading dislocation density, according to at least one example embodiment.

FIG. 5 is a graph showing the correlation between V-pit density and TDD. In FIG. 5, the X-axis represents V-pit density VD, and the Y-axis represents TDD. In FIG. 5, like reference numerals that are the same as those of FIGS. 1 through 4B represent like elements, and for simplicity of explanation, a redundant description thereof will be omitted.

Referring to FIG. 5, a second TDD, TDD2 is the TDD of the wafer 20 at a time corresponding to the second V-pit density VD2. That is, TDD2 is the TDD of the wafer 20 that corresponds to the second reflectance difference ΔR_2. Similarly, TDD3 and TDD4 are the TDDs of the wafer 20 at time intervals T1_3 and T1_4 that correspond to the third and fourth V-pit densities VD3 and VD4.

In terms of the relationship between the second through fourth V-pit densities VD2, VD3, and VD4 and TDD2, TDD3, and TDD4 obtained through experiments, TDD2 when the second V-pit density VD2 is $2.53 \times 10^8/cm^2$, is $2.5 \times 10^8/cm^2$, TDD3 when the third V-pit density VD3 is $5.12 \times 10^8/cm^2$, is $5.1 \times 10^8/cm^2$, and TDD4 when the fourth V-pit density VD4 is $7.13 \times 10^8/cm^2$, is $7.1 \times 10^8/cm^2$. That is, the TDD may be in proportion to the V-pit density VD (Equation 2). k2 in Equation 2 is a constant reflecting proportionality.

$$TDD = k2 \cdot VD \qquad [\text{Equation 2}]$$

Through the above-described Equations 1 and 2, Equation 3 may be obtained. k in Equation 3 is a constant reflecting proportionality.

$$TDD = k \cdot \Delta R \qquad [\text{Equation 3}]$$

In Equation 3, the constant k may vary depending on the composition of a compound semiconductor grown on the wafer 20, an area of a V-pit formed in the wafer 20, an inclination angle of a V-pit formed in the wafer 20, and the number of layers of a crystal growth layer formed on the wafer 20.

The constant k may be obtained from a sample wafer by using a method, such as X-ray diffraction (XRD) analysis or cathodoluminescence (CL) analysis.

Here, XRD analysis is a technique for measuring a degree of asymmetry of a crystal lattice by using a diffraction strength of X rays. CL analysis is a measurement technique using a phenomenon where accelerated electron beams are applied to the sample wafer and applied energy is converted into light in the sample wafer and dissipated. CL analysis is a technique for evaluating the quality of the crystal from a feature in which light is not emitted from a region in which dislocation is present.

Consequently, from the correlation (Equation 3) between the TDD and the reflectance difference ΔR, the data processing unit 120 may measure the reflectance difference ΔR that is measured in a particular time interval (T1 of FIG. 4A) until a V-pit is intentionally formed, among time intervals in which the wafer 20 is grown in the growth chamber 130 and in a particular time interval (a particular time interval selected from T1_1 through T1_5 of FIG. 4A), thereby calculating the TDD according to each particular time interval.

Figure 6A:
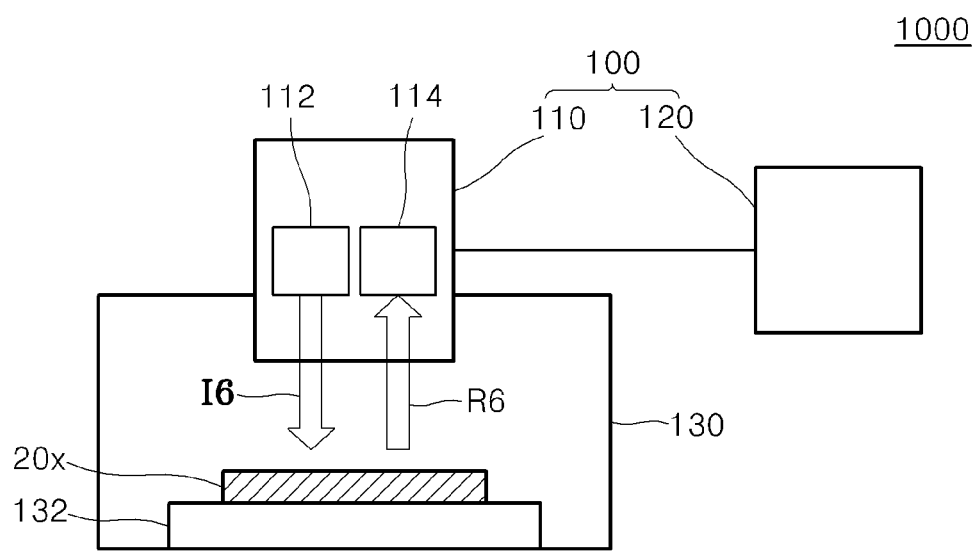
FIGS. 6A and 6B are schematic views illustrating a principle that reflectance is reduced when a V-pit is formed in a surface of a wafer during growth of the wafer, according to at least one example embodiment.
Figure 6B:
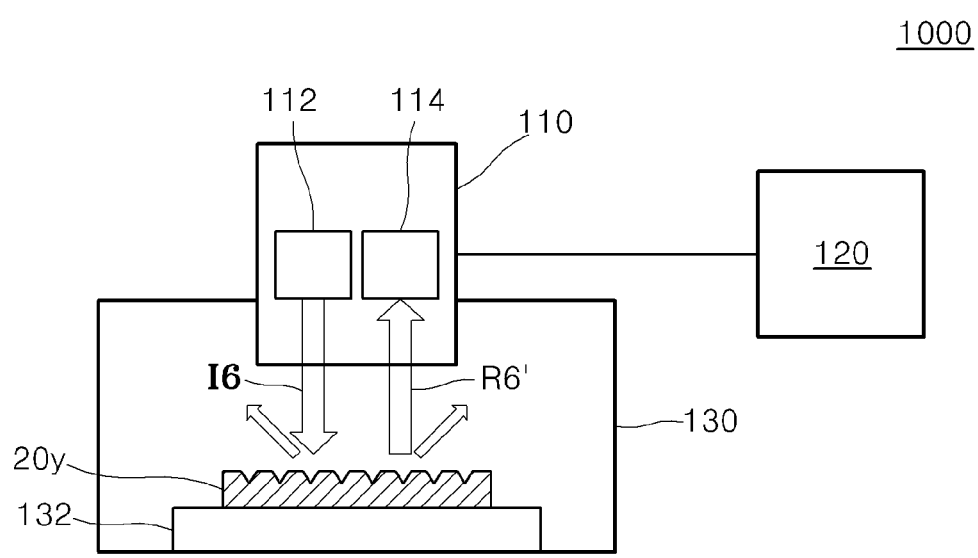

FIGS. 6A and 6B are schematic views illustrating the reduction of reflectance when a V-pit is formed in a surface of a wafer during growth of the wafer. In FIGS. 6A and 6B, like reference numerals that are the same as those of FIGS. 1 through 5 represent like elements, and for simplicity of explanation, a redundant description thereof will be omitted.

Referring to FIG. 6A, the apparatus 100 for evaluating the quality of the crystal measures the surface reflectance of a wafer 20x that is being grown in the growth chamber 130.

According to at least one example embodiment, the wafer 20x is formed by stacking the first conductive layer 23, a pit layer 24, the active layer 25, and the second conductive layer 27 on a base substrate 11 (see FIG. 7B). Here, the wafer 20x is a wafer in which only the first conductive layer 23 is formed on the base substrate 11 and no pit layer 24, no active layer 25 and no second conductive layer 27 are formed.

In this case, a surface of the wafer 20x, i.e., a surface of the first conductive layer 23, constitutes a substantially planar structure. Thus, when incident light I6 radiated by the light-emitting unit 112 is in a direction perpendicular to the surface of the wafer 20x, a quantity of scattered incident light I6 is not large so that a quantity of incident light I6 and a quantity of reflected light R6 are not substantially different from each other.

Referring to FIG. 6B, the apparatus 100 for evaluating the quality of a crystal measures the surface reflectance of a wafer 20y that is being grown in the growth chamber 130.

Here, the wafer 20y is a wafer in which, after formation of the first conductive layer 23 is finished on the base substrate 11, the pit layer 24 is formed or the wafer 20y is being grown after formation of the pit layer 24 is formed.

In this case, a V-pit structure V is formed in a surface of the wafer 20y, i.e., in a surface of the pit layer 24. Thus, even when incident light I6 radiated by the light-emitting unit 112 is in a direction perpendicular to the surface of the wafer 20y, the incident light I6 is scattered by the V-pit structure V in the surface of the wafer 20y, and a quantity of reflected light R6' in FIG. 6B is smaller than a quantity of reflected light R6 of FIG. 6A. Thus, the surface reflectance of the wafer 20y is smaller than the surface reflectance of the wafer 20x.

FIGS. 7A and 7B are schematic views illustrating why a V-pit is formed when a nitride-based semiconductor is grown. In FIGS. 7A and 7B, like reference numerals that are the same as those of FIGS. 1 through 6B represent like elements, and for simplicity of explanation, a redundant description thereof will be omitted.

Referring to FIG. 7A, a wafer 10 includes a base substrate 11, a first conductive layer 13, an active layer 15, and a second conductive layer 17.

The base substrate 11 may be a conductive substrate or an insulating substrate. For example, the base substrate 11 may include at least one of sapphire ($Al_2O_3$), silicon (Si), silicon carbide (SiC), gallium arsenide (GaAs), gallium nitride (GaN), zinc oxide (ZnO), gallium phosphorous (GaP), indium phosphorous (InP), and germanium (Ge). The base substrate 11 may be wet washed so that impurities may be removed from a surface of the base substrate 11. The base substrate 11 may be a patterned substrate (PSS), of which a surface is patterned so as to enhance light extraction efficiency. However, example embodiments are not limited thereto.

The first conductive layer 13 may be formed on the base substrate 11. The first conductive layer 13 may include a semiconductor material having a composition formula $Al_xIn_yGa_{(1-x-y)}N$ ($0 \leq x \leq 1$, $0 \leq y \leq 1$, $0 \leq x+y \leq 1$), for example, at least one of GaN, InN, AlN, InGaN, AlGaN, InAlGaN, and AlInN. Also, the first conductive layer 13 may be formed using another group V element instead of N. For example, the first conductive layer 13 may include at least one of AlGaAs, InGaAs, AlInGaAs, GaP, AlGaP, InGaP, AlInGaP, and InP. When the first conductive layer 13 is an n-type conductive layer, the first conductive layer 13 may include Si, Ge, Sn, Se, and Te as n-type impurities.

A buffer layer (not shown) that alleviates lattice mismatch between the base substrate 11 and the first conductive layer 13 and causes the first conductive layer 13 to be easily grown may be additionally interposed between the base substrate 11 and the first conductive layer 13. The buffer layer (not shown) may be formed to have a stack structure of AlInN/GaN, a stack structure of InGaN/GaN, or a stack structure of AlInGaN/InGaN/GaN including AlN and GaN.

The active layer 15 may be formed on the first conductive layer 13. The active layer 15 is a region in which electrons and holes are re-combined. The active layer 15 may be transited to a low energy level as the electrons and the holes are re-combined and may generate light having a wavelength corresponding to the low energy level. The active layer 15 may include a semiconductor material having a composition formula, for example, $In_xAl_yGa_{(1-x-y)}N$ ($0 \leq x \leq 1$, $0 \leq y \leq 1$, $0 \leq x+y \leq 1$). The active layer 15 may have a single quantum well structure or a multi quantum well (MQW) structure. Thus, more electrons are collected at a low energy level of a quantum well layer. As such, a possibility that the electrons and the holes may be re-combined is increased so that a luminescent effect may be enhanced. Also, the active layer 15 may have a quantum wire structure or a quantum dot structure.

The second conductive layer 17 may be formed on the active layer 15. The second conductive layer 17 may be implemented as a p-type conductive layer and may provide holes to the active layer 15. For example, the p-type conductive layer may include a semiconductor material having a composition formula $In_xAl_yGa_{(1-x-y)}N$ ($0 \leq x \leq 1$, $0 \leq y \leq 1$, $0 \leq x+y \leq 1$), for example, one of GaN, AlN, AlGaN, InGaN, InN, InAlGaN, and AlInN and may be doped with a p-type impurity, such as Mg, Zn, Ca, Sr, or Ba.

In some example embodiments, the first conductive layer 13, the active layer 15, and the second conductive layer 17 described above may be formed using techniques, such as MOCVD, MBE, HVPE, chemical vapor deposition (CVD), plasma-enhanced chemical vapor deposition (PECVD), and sputtering.

In the growth of the wafer 10 having the nitride-based epitaxial layer as described above, the base substrate 11 may be different from the first conductive layer 13, the active layer 15, and the second conductive layer 17 and is formed at a density at which threading dislocation (TD) is high. A dislocation region Xa in which TD is formed has a lower energy barrier than the energy barrier of a non-dislocation region Ya in which no TD is formed, so that non-emission re-combination of the electrons is induced and a luminous intensity of a light-emitting device is reduced.

Referring to FIG. 7B, the wafer 20 includes the base substrate 11, the first conductive layer 23, the pit layer 24, the active layer 25, and the second conductive layer 27.

The first conductive layer 23 may be formed on the base substrate 11. The first conductive layer 23 may include a semiconductor material having a composition formula $Al_xIn_yGa_{(1-x-y)}N$ ($0 \leq x \leq 1$, $0 \leq y \leq 1$, $0 \leq x+y \leq 1$). When the first conductive layer 23 is an n-type conductive layer, the first conductive layer 23 may include Si, Ge, Sn, Se, or Te as an n-type impurity.

A buffer layer (not shown) may be additionally interposed between the base substrate 11 and the first conductive layer 23. The buffer layer may have a stack structure of AlInN/GaN, InGaN/GaN, or AlInGaN/InGaN/GaN including AlN and GaN.

The pit layer 24 may be formed on the first conductive layer 23. In some example embodiments, the pit layer 24 may be formed of the same material as the first conductive layer 23. However, example embodiments are not limited thereto, and the pit layer 24 may include least one of GaN, InN, AlN, InGaN, AlGaN, InAlGaN, and AlInN.

The pit layer 24 may have a V-pit structure V. The V-pit structure V may be formed when a growth temperature of the pit layer 24 is lower than the growth temperature of the first conductive layer 23. However, example embodiments of the inventive concepts are not limited thereto, and the V-pit structure V may be formed using various methods.

The V-pit structure V may be formed based on TD. Thus, a density VD of a V-pit formed under the same conditions (in particular, temperature and time) is in proportion to TDD (see FIG. 5).

The active layer 25 may be formed on the pit layer 24. The active layer 25 may have a V-pit structure corresponding to the V-pit structure V formed in the pit layer 24. The active layer 25 may include a semiconductor material having a composition formula $In_xAl_yGa_{(1-x-y)}N$ ($0 \leq x \leq 1$, $0 \leq y \leq 1$, $0 \leq x+y \leq 1$), for example, and may have a single quantum well structure or an MQW structure.

The second conductive layer 27 may be formed on the active layer 25. The second conductive layer 27 may have a V-pit structure corresponding to the V-pit structure formed in the active layer 25. The second conductive layer 27 may be implemented as a p-type conductive layer and may provide holes to the active layer 25. For example, the second conductive layer 27 may include a semiconductor material having a composition formula $In_xAl_yGa_{(1-x-y)}N$ ($0 \leq x \leq 1$, $0 \leq y \leq 1$, $0 \leq x+y \leq 1$) and may be doped with a p-type impurity, such as Mg, Zn, Ca, Sr, or Ba.

As described above, the V-pit structure V is formed in a dislocation region Xb in which TD of the wafer 20 is formed. Thus, the dislocation region Xb may have a higher energy barrier than the energy barrier of the dislocation region (Xa of FIG. 7A) so that non-emission re-combination of electrons described above may be prevented and a luminous intensity of a light-emitting device may be enhanced.

Figure 8A:
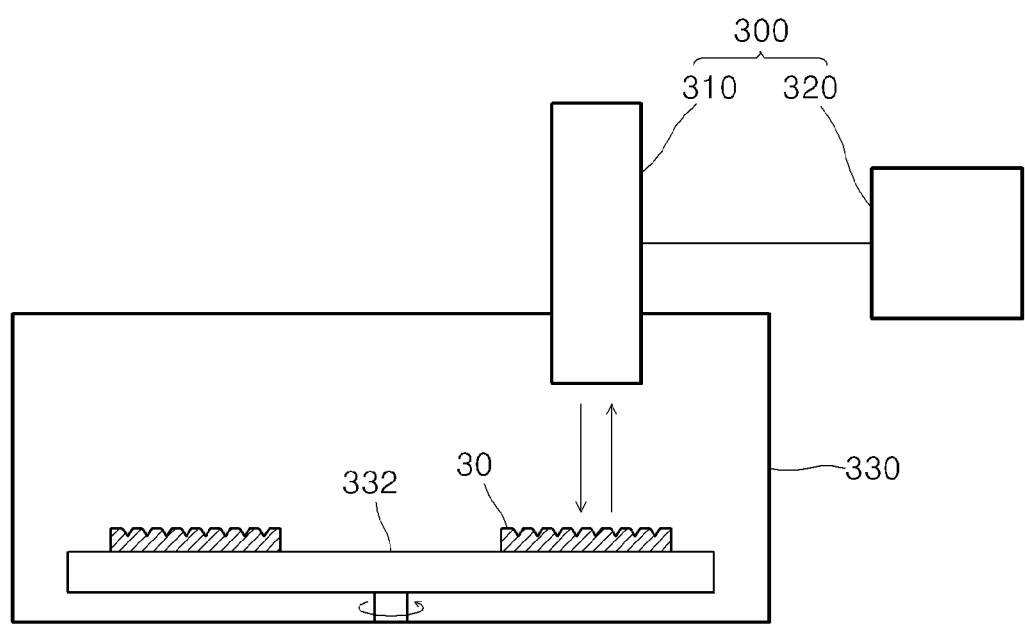
FIG. 8A schematically illustrates part of a configuration of an apparatus for manufacturing a semiconductor light-emitting device including an apparatus for evaluating the quality of a crystal, according to another example embodiment.

FIG. 8A schematically illustrates part of a configuration of an apparatus 3000 for manufacturing a semiconductor light-emitting device including an apparatus 300 for evaluating quality of crystal, according to another example embodiment.

Figure 8B:
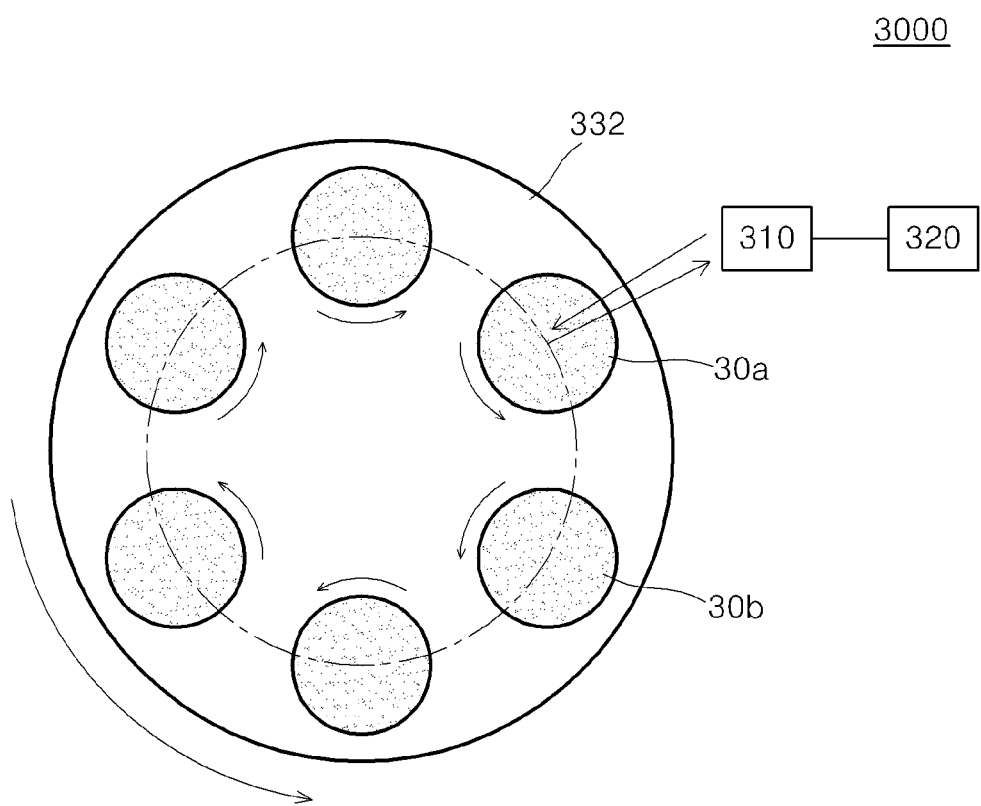
FIG. 8B is a plan view conceptually illustrating a state in which an apparatus for manufacturing a semiconductor light-emitting device is used in a plurality of wafers, according to an example embodiment.

FIG. 8B is a plan view conceptually illustrating a state in which the apparatus 3000 for manufacturing a semiconductor light-emitting device is used on a plurality of wafers, according to an example embodiment. In FIGS. 8A and 8B, like reference numerals that are the same as those of FIGS. 1 and 7B represent like elements, and for simplicity of explanation, a redundant description thereof will be omitted.

Referring to FIG. 8A, the apparatus 3000 for manufacturing a semiconductor light-emitting device includes the apparatus 300 for evaluating quality of crystal and a growth chamber 330 that is connected to an optical device 310 of the apparatus 300 for evaluating quality of crystal.

The apparatus 300 for evaluating quality of crystal includes the optical device 310 and a data processing unit 320 that processes data received from the optical device 310.

The optical device 310 according to the example embodiment is disposed above the growth chamber 330. However, example embodiments are not limited thereto, and the optical device 310 may be disposed at a side of the growth chamber 330. Also, as illustrated in FIG. 8A, part of the optical device 310 may not be disposed in the growth chamber 330 and the optical device 310 may be spaced apart from the growth chamber 330 (not shown). In this case, incident light and reflected light of the optical device 310 pass through a transparent window (not shown) installed at the growth chamber 330.

In some example embodiments, the optical device 310 of the apparatus 300 for evaluating quality of crystal is disposed to correspond to a growth surface of a plurality of wafers 30 and evaluates the quality of crystal of the plurality of wafers 30 that are being grown.

In some example embodiments, the apparatus 300 for evaluating quality of crystal evaluates the quality of crystal of the plurality of wafers 30 in real-time while the plurality of wafers 30 are grown in the growth chamber 330.

In some example embodiments, in the growth chamber 330, the plurality of wafers 30 may be grown using MOCVD, MBE, or HVPE. The growth chamber 330 includes a wafer chuck 332 that supports the plurality of wafers 30 while the wafers 30 are grown. Although not shown, the growth chamber 330 may further include a gas supply pipe, a gas exhaust pipe, and a heating unit, in addition to the wafer chuck 332.

The wafer chuck 332 may be rotated in a desired, or alternatively, predetermined direction while the plurality of wafers 30 are grown. In some example embodiments, the wafer chuck 332 may be rotated and simultaneously or contemporaneously, the plurality of wafers 30 may also be rotated. A direction in which the plurality of wafers 30 are rotated may be the same as a direction in which the wafer chuck 332 is rotated.

While the plurality of wafers 30 are grown, the optical device 310 in a fixed state sequentially performs a reflectance measurement on each of the plurality of wafers 30. For example, when a wafer 30a is disposed to correspond to the optical device 310, the optical device 310 performs a reflectance measurement on the wafer 30a, and when a wafer 30b is disposed to correspond to the optical device 310, the optical device 310 performs a reflectance measurement on the wafer 30b.

In some example embodiments, the data processing unit 320 collects the surface reflectance of the plurality of wafers 30 in a particular time interval and calculates the total difference in the surface reflectance for each of the plurality of wafers 30 in the particular time interval. The data processing unit 320 may calculate a density of a V-pit formed in each of the plurality of wafers 30 by using the calculated difference in surface reflectance for each of the plurality of wafers 30.

In some example embodiments, the data processing unit 320 may calculate TDD of each of the plurality of wafers 30 by using the calculated density of the V-pit.

Figure 9A:
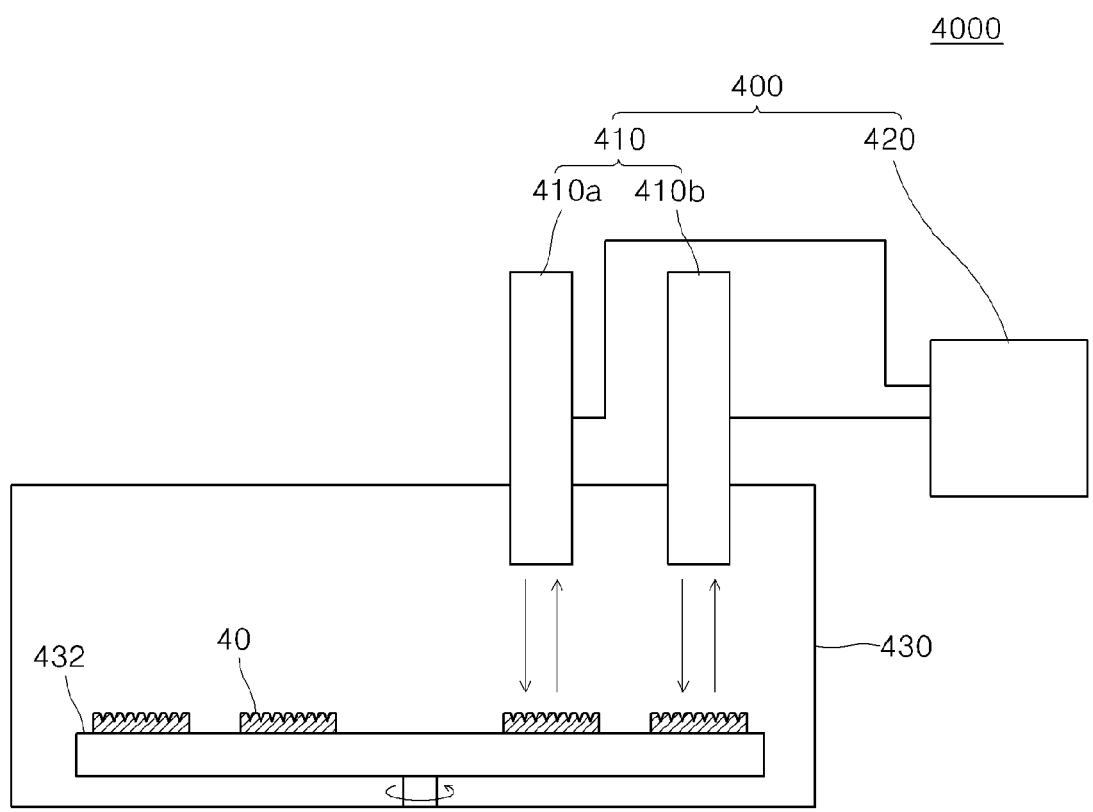
FIG. 9A schematically illustrates part of a configuration of an apparatus for manufacturing a semiconductor light-emitting device including an apparatus for evaluating the quality of a crystal, according to another example embodiment.
Figure 9B:
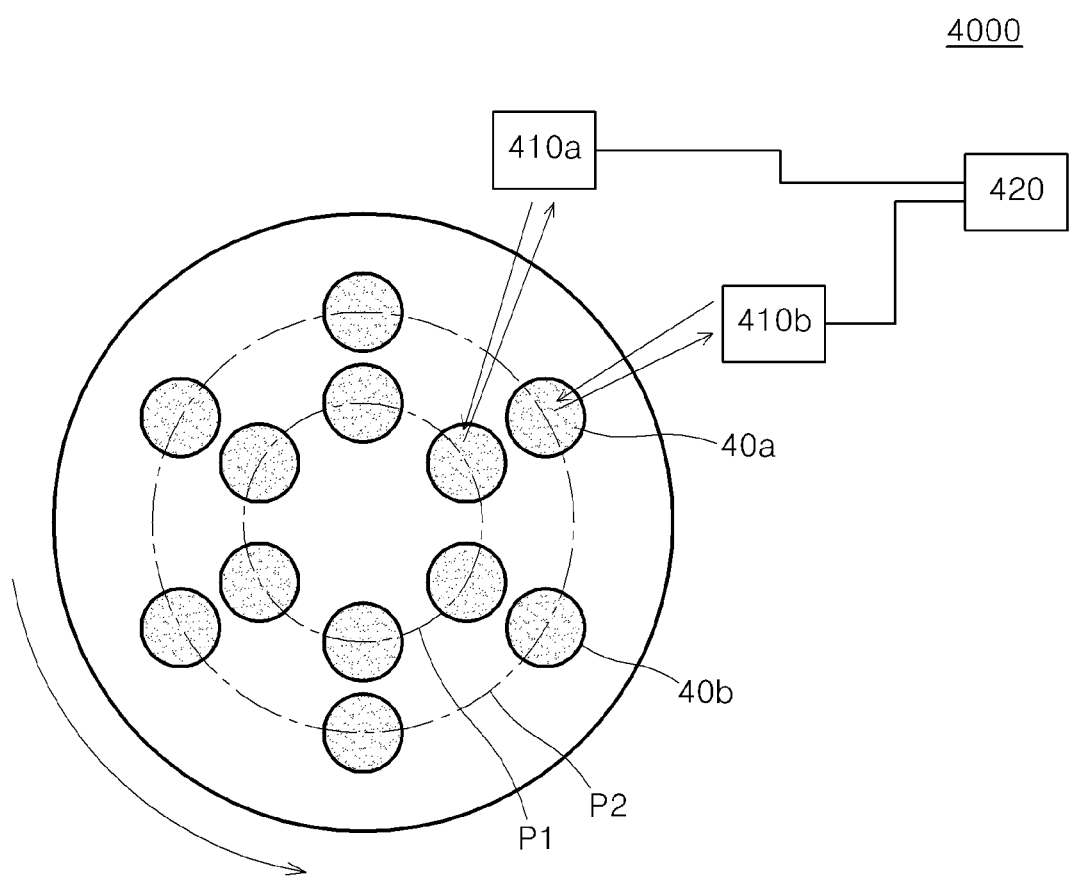
FIG. 9B is a plan view conceptually illustrating a state in which an apparatus for manufacturing a semiconductor light-emitting device is used in a plurality of wafers, according to another example embodiment.

FIG. 9A schematically illustrates part of a configuration of an apparatus 4000 for manufacturing a semiconductor light-emitting device including an apparatus 400 for evaluating quality of crystal, according to another example. FIG. 9B is a plan view conceptually illustrating a state in which the apparatus 4000 for manufacturing a semiconductor light-emitting device is used on a plurality of wafers, according to another example embodiment. In FIGS. 9A and 9B, like reference numerals that are the same as those of FIGS. 1 through 8B represent like elements, and for simplicity of explanation, a redundant description thereof will be omitted.

Referring to FIG. 9A, the apparatus 4000 for manufacturing a semiconductor light-emitting device includes the apparatus 400 for evaluating quality of crystal and a growth chamber 430 that is connected to an optical device 410 of the apparatus 400 for evaluating quality of crystal.

The apparatus 400 for evaluating the quality of a crystal includes the optical device 410 and a data processing unit 420 that processes data received from the optical device 410.

The optical device 410 according to the example embodiment is disposed above the growth chamber 430. However, example embodiments are not limited thereto, and the optical device 410 may be disposed at a side of the growth chamber 430. Also, as illustrated in FIG. 9A, part of the optical device 410 may not be disposed in the growth chamber 430 and the optical device 410 may be spaced apart from the growth chamber 430 (not shown). In this case, incident light and reflected light of the optical device 410 pass through a transparent window (not shown) installed at the growth chamber 430.

The optical device 410 includes a first optical device 410a that measures the reflectance of a wafer rotating along a path P1 among a plurality of wafers 40, and a second optical device 410b that measures the reflectance of a wafer rotating along path P2 among the plurality of wafers 40. In some example embodiments, the optical device 410a corresponds to a growth surface of a wafer rotating along a path P1 among the plurality of wafers 40 and evaluates the quality of crystal of the wafer rotating along the path P1. The optical device 410b corresponds to a growth surface of a wafer rotating along a path P2 among the plurality of wafers 40 and evaluates the quality of crystal of the wafer rotating along the path P2. The optical device 410b corresponds to a growth surface of the wafer rotating along the path P2 among the plurality of wafers 40 and evaluates the quality of crystal of the wafer rotating along the path P2.

In some example embodiments, the apparatus 400 for evaluating quality of crystal is configured to evaluate the quality of crystal of the plurality of wafers 40 in real-time while the plurality of wafers 40 are grown in the growth chamber 430. In the growth chamber 430, the plurality of wafers 40 may be grown using MOCVD, MBE, and HVPE. The growth chamber 430 includes a wafer chuck 432 that supports the plurality of wafers 40 while the wafers 40 are grown. Although not shown, the growth chamber 430 may further include a gas supply pie, a gas exhaust pipe, and a heating unit, in addition to the wafer chuck 432.

The wafer chuck 432 may be configured to rotate in a predetermined direction while the plurality of wafers 40 are grown. In some example embodiments, the wafer chuck 432 may be rotated and simultaneously or contemporaneously, each of the plurality of wafers 40 may be rotated. A direction in which the plurality of wafers 40 are rotated may be the same as a direction in which the wafer chuck 432 is rotated.

While the plurality of wafers 40 are grown, the optical device 410 in a fixed state is configured to sequentially perform a reflectance measurement on each of the plurality of wafers 40. For example, when a wafer 40a corresponds to the second optical device 410b, the second optical device 410b is configured to perform a reflectance measurement on the wafer 40a, and when a wafer 40b corresponds to the second optical device 410b, the second optical device 410b is configured to perform a reflectance measurement on the wafer 40b.

According to at least one example embodiment, the data processing unit 420 is connected to each of the first optical device 410a and the second optical device 410b and collects the reflectance of each of the plurality of wafers 40 measured by the first optical device 410a and the second optical device 410b, thereby calculating TDD.

In some example embodiments, the data processing unit 420 collects the surface reflectance of the plurality of wafers 40 in a particular time interval and calculates the total difference in surface reflectance of each of the plurality of wafers 40 in the particular time interval. The data processing unit 420 may calculate a density of a V-pit formed in each of the plurality of wafers 40 by using the calculated difference in surface reflectance of each of the plurality of wafers 40.

In some example embodiments, the data processing unit 420 may calculate TDD of each of the plurality of wafers 40 by using the calculated density of the V-pit.

Figure 10:
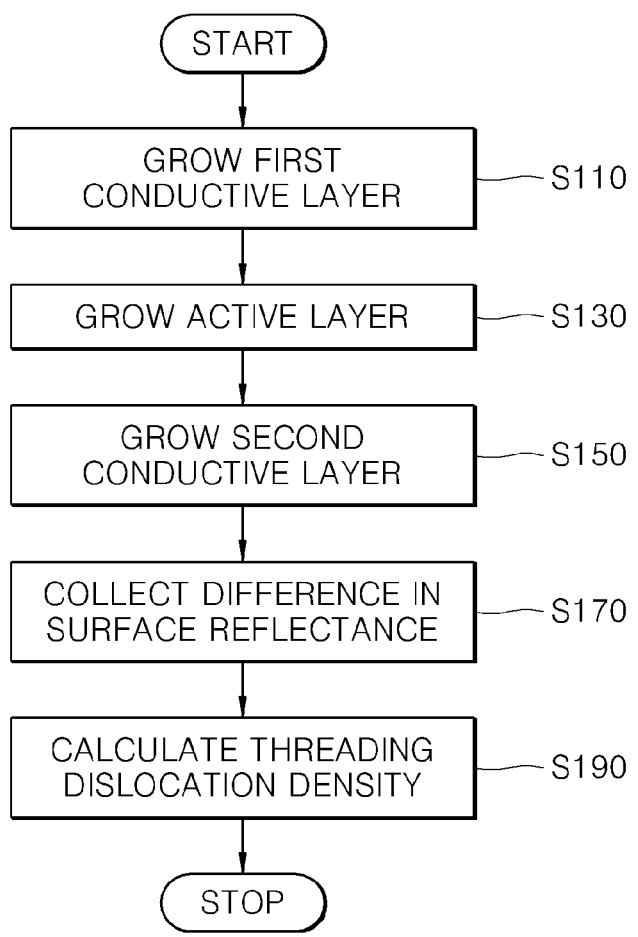
FIG. 10 is a flowchart of a method of manufacturing a semiconductor light-emitting device, according to an example embodiment.

FIG. 10 is a flowchart of a method of manufacturing a semiconductor light-emitting device, according to an example embodiment of the inventive concepts.

Referring to FIGS. 10 and 7B, the method of manufacturing the semiconductor light-emitting device includes growing a wafer 20 for the semiconductor light-emitting device including the first conductive layer 23, the active layer 25 and the second conductive layer 27 so that a V-pit may be formed in at least one layer from the first conductive layer 23, the active layer 25, and the second conductive layer 27. In detail, the example method of manufacturing the semiconductor light-emitting device further includes growing the first conductive layer 23 on the base substrate 11 (S110), growing the active layer 25 (5130), and growing the second conductive layer 27 (S150).

In FIG. 7B, no V-pit V is formed in the first conductive layer 23. However, example embodiments are not limited thereto, and similar to the active layer 23 and the second conductive layer 27a, a V-pit may be formed in the first conductive layer 23.

On the other hand, in a growth step of the wafer 20, the optical device (see 110 of FIG. 1) measures the surface reflectance of one or more layers from the first conductive layer 23, the active layer 25 and the second conductive layer 27, which are being grown on the wafer 20. The surface reflectance may be continuously measured while the first conductive layer 23, the active layer 25 and the second conductive layer 27 are grown. The surface reflectance may be measured only in a particular time zone and may be discontinuously or intermittently measured when the first conductive layer 23, the active layer 25 and the second conductive layer 27 are arbitrarily selected.

Thereafter, the example method of manufacturing the semiconductor light-emitting device further includes calculating a difference of the measured surface reflectance (S170) and calculating TDD from the collected data (S190) so that quality of crystal of the wafer 20 for the semiconductor light-emitting device may be evaluated.

For example, the optical device 110 measures the surface reflectance of the first conductive layer 23 in operation S110 in which the first conductive layer 23 is grown before a V-pit V is formed and measures the surface reflectance of the second conductive layer 27 in operation S150 in which the second conductive layer 27 is grown while a V-pit V is formed and then, the data processing unit 120 collects the measured surface reflectance after the surface reflectance of the second conductive layer 27 is measured. The data processing unit 120 may calculate a difference in the measured surface reflectance in operation S110 in which the first conductive layer 23 is grown before a V-pit V is formed and in operation S150 in which the second conductive layer 27 is grown while a V-pit V is formed and may calculate TDD by using the calculated difference in the surface reflectance. However, unlike in the above example, when there is surface reflectance data before a V-pit V is formed, an operation in which surface reflectance is measured before a V-pit V is formed, may be omitted. Also, in the above example, a V-pit V is formed in operation S150 in which the second conductive layer 27 is grown. However, example embodiments are not limited thereto. The V-pit V may be formed in one or more layer selected from the first conductive layer 23, the active layer 25 and the second conductive layer 27 of the wafer 20.

While the inventive concepts have been particularly shown and described with reference to example embodiments thereof, it will be understood that various changes in form and details may be made therein without departing from the spirit and scope of the following claims.

What is claimed is:

1. A method of manufacturing a semiconductor light-emitting device, the method comprising:
    growing a wafer so that a surface feature is formed in one or more layers of the wafer for the semiconductor light-emitting device, the wafer including a first conductive layer, an active layer, and a second conductive layer;
    measuring a surface reflectance of one or more of the first conductive layer, the active layer, and the second conductive layer of the wafer using an optical device during the growing of the wafer; and
    evaluating a quality of crystal by calculating a difference of the measured surface reflectance over a time interval and by calculating a threading dislocation density of the wafer.

2. The method of claim 1, wherein the measuring of the surface reflectance comprises:
    radiating incident light onto the wafer; and
    receiving reflected light from the wafer.

3. The method of claim 2, wherein the measuring of the surface reflectance further comprises one of changing a path of the incident light or the reflected light and focusing the incident light or the reflected light.

4. The method of claim 2, wherein the incident light is in a wavelength area in which no Fabry-Perot interference occurs.

5. The method of claim 2, wherein a wavelength of the incident light is substantially between 300 nm and 420 nm.

6. The method of claim 1, wherein the evaluating comprises:
    measuring a surface reflectance of the wafer during the time interval; and
    calculating a threading dislocation density of the wafer by using the difference in the surface reflectance collected during the time interval.

* * * * *